United States Patent [19]

Jeffery et al.

[11] Patent Number: 4,767,790

[45] Date of Patent: * Aug. 30, 1988

[54] THERAPEUTIC AGENTS

[75] Inventors: James E. Jeffery; Antonin Kozlik; Eric C. Wilmshurst, all of Nottingham, Great Britain

[73] Assignee: The Boots Company plc, England

[*] Notice: The portion of the term of this patent subsequent to Jun. 11, 2002 has been disclaimed.

[21] Appl. No.: 725,129

[22] Filed: Apr. 19, 1985

Related U.S. Application Data

[63] Continuation of Ser. No. 365,285, Apr. 5, 1982, Pat. No. 4,522,828.

[30] Foreign Application Priority Data

Apr. 6, 1981 [GB] United Kingdom ................. 8110709

[51] Int. Cl.$^4$ ............................................. C07C 87/50
[52] U.S. Cl. ................................... 514/646; 564/305; 514/247; 514/277; 514/359; 514/408; 544/403; 546/348; 546/346; 548/578
[58] Field of Search ........................ 564/305; 544/403; 546/346, 348; 548/578; 514/646, 247, 277, 359, 408

[56] References Cited

U.S. PATENT DOCUMENTS 4,443,449  4/1984  Jeffery et al. .................. 514/646 X
4,522,828  6/1985  Jeffery et al. .................. 514/247 X Primary Examiner—Paul F. Shaver
Attorney, Agent, or Firm—Jacobs & Jacobs

[57] ABSTRACT

Compounds of formula I

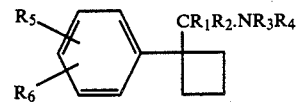

in which $R_1$ is $C_{1-6}$ alkyl, $C_{2-6}$ alkenyl, $C_{2-6}$ alkynyl, $C_{3-7}$ cycloalkyl, cycloalkylalkyl or optionally substituted phenyl; $R_2$ is H or $C_{1-3}$ alkyl; $R_3$ and/or $R_4$ are H, formyl, $C_{1-3}$ alkyl, $C_{3-6}$ alkenyl, $C_{3-6}$ alkynyl, $C_{3-7}$ cycloalkyl or $R_3$ and $R_4$ together with the nitrogen atom form a heterocyclic ring system; $R_5$ and/or $R_6$ are H, halo, $CF_3$, $C_{1-3}$ alkyl, $C_{1-3}$ alkoxy, $C_{1-3}$ alkylthio or $R_5$ and $R_6$ together with the carbon atoms to which they are attached form a second benzene ring show therapeutic acitivity in the treatment of depression. Pharmaceutical compositions and processes for preparing compounds of formula I are disclosed.

22 Claims, No Drawings

THERAPEUTIC AGENTS

This is a continuation of application Ser. No. 365,285, filed Apr. 5, 1982, now U.S. Pat. No. 4,522,828.

This invention relates to compounds having useful therapeutic activity as antidepressants, to pharmaceutical compositions containing such compounds and to processes for the preparation of such compounds.

The present invention provides compounds of formula I

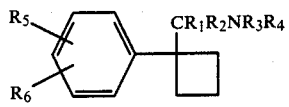

in which $R_1$ is a straight or branched chain alkyl group containing 1 to 6 carbon atoms, a cycloalkyl group containing 3 to 7 carbon atoms, a cycloalkylalkyl group in which the cycloalkyl group contains 3 to 6 carbon atoms and the alkyl group contains 1 to 3 carbon atoms, an alkenyl group or an alkynyl group containing 2 to 6 carbon atoms or a group of formula II

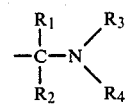

in which $R_9$ and $R_{10}$, which may be the same or different, are H, halo or an alkoxy group containing 1 to 3 carbon atoms;
in which $R_2$ is H or an alkyl group containing 1 to 3 carbon atoms;
in which $R_3$ and $R_4$, which may be the same or different, are H, a straight or branched chain alkyl group containing 1 to 4 carbon atoms, an alkenyl group having 3 to 6 carbon atoms, an alkynyl group having 3 to 6 carbon atoms, a cycloalkyl group in which the ring contains 3 to 7 carbon atoms, a group of formula $R_{11}CO$ where $R_{11}$ is H or $R_3$ and $R_4$ together with the nitrogen atom to which they are attached form an optionally substituted heterocyclic ring having 5 or 6 atoms in the ring which may contain further hetero atoms in addition to the nitrogen atom: in which $R_5$ and $R_6$, which may be the same or different, are H, halo, trifluoromethyl, an alkyl group containing 1 to 3 carbon atoms, an alkoxy or alkylthio group containing 1 to 3 carbon atoms, phenyl, or $R_5$ and $R_6$, together with the carbon atoms to which they are attached, form a second benzene ring which may be substituted by one or more halo groups, an alkyl or alkoxy group containing 1 to 4 carbon atoms or the substituents of the second benzene ring together with the two carbon atoms to which they are attached may form a further benzene ring;
and their pharmaceutically acceptable salts.

In the formulae included in this specification the symbol

represents a 1,1-disubstituted cyclobutane group of formula

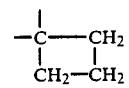

and $-CR_1R_2.NR_3R_4$ represents a group of formula

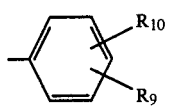

In the preferred compounds of formula I $R_1$ is a straight or branched chain alkyl group containing 1 to 4 carbon atoms, a cycloalkyl group containing 3 to 7 carbon atoms, a cycloalkylmethyl group in which the cycloalkyl ring contains 3 to 6 carbon atoms or a group of formula II in which $R_9$ and/or $R_{10}$ are H, fluoro or methoxy and in which $R_2$ is H or methyl. Examples of particularly preferred compounds of formula I are those in which $R_2$ is H and $R_1$ is methyl, ethyl, propyl, isopropyl, butyl, sec-butyl, isobutyl cyclopropyl, cyclobutyl, cyclopentyl, cyclohexyl, cycloheptyl, cyclopropylmethyl, cyclobutylmethyl, cyclopentylmethyl, cyclohexylmethyl or phenyl.

In preferred compounds of formula I, $R_3$ and/or $R_4$ are hydrogen, methyl, ethyl or formyl or $R_3$ and $R_4$ together with the nitrogen atom to which they are attached form a heterocyclic ring containing one nitrogen atom and 4 or 5 carbon atoms which is optionally substituted by one or more alkyl groups or $R_3$ and $R_4$ together with the nitrogen atom to which they are attached form a heterocyclic ring containing a second nitrogen atom which is optionally alkylated or a heterocyclic ring including one or more double bonds.

In preferred compounds of formula I $R_5$ and/or $R_6$ are H, fluoro, chloro, bromo, iodo, trifluoromethyl, methyl, methoxy, phenyl or $R_5$ and $R_6$ together with the carbon atoms to which they are attached form a second benzene ring which may optionally be substituted by halo.

A first group of preferred compounds of formula I is represented by formula III

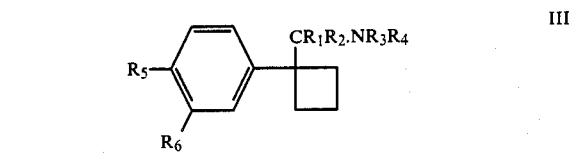

in which $R_5$ and $R_6$ are as defined above. In preferred compounds of formula III $R_5$ and $R_6$, which may be the same or different, are H, fluoro, chloro, bromo, iodo, trifluoromethyl, methyl, methoxy, phenyl or in which $R_5$ and $R_6$ together with the carbon atoms to which they are attached form a second benzene ring which may optionally be substituted by a chloro group. In particularly preferred compounds of formula III $R_5$ and/or $R_6$ are H, fluoro, chloro, iodo, trifluoromethyl, methyl, phenyl or $R_5$ and $R_6$ together with the carbon atoms to which they are attached form a second benzene ring which may optionally be substituted by a chloro group.

A second group of preferred compounds of formula I· is represented by formula IV

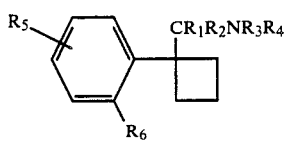

in which $R_5$ may be H, fluoro, chloro, bromo, iodo, trifluoromethyl, methyl, methoxy or phenyl and in which $R_6$ is fluoro or methyl. In particular preferred compounds of formula IV $R_5$ is H or chloro.

Compounds of formula I may exist as salts with pharmaceutically acceptable acids. Examples of such salts include hydrochlorides, maleates, acetates, citrates, fumarates, tartrates, succinates and salts with acidic amino acids such as aspartic and glutamic acids.

Compounds of formula I which contain one or more asymmetric carbon atoms can exist in different optically active forms. When $R_1$ and $R_2$ are different or $R_7$ and $R_8$ are different, the compounds of formula I contain a chiral centre. Such compounds exist in two enantiomeric forms and the present invention includes both enantiomeric forms and mixtures thereof. When $R_1$ and $R_2$ are different and $R_1$ contains a chiral centre the compounds of formula I contain two chiral centres and the compounds exist in four diastereoisomeric forms. The present invention includes each of these diastereoisomeric forms and mixtures thereof.

The present invention also includes pharmaceutical compositions containing a therapeutically effective amount of a compound of formula I together with a pharmaceutically acceptable diluent or carrier.

In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–90% by weight of active compound. The compositions of the invention are generally prepared in unit dosage form.

Compositions for oral administration are the preferred compositions of the invention and these are the known pharmaceutical forms for such administration, for example tablets, capsules, syrups and aqueous or oily suspensions. The excipients used in the preparation of these compounds are the excipients known in the pharmacists' art. Tablets may be prepared by mixing the active compound with an inert diluent such as calcium phosphate in the presence of disintegrating agents, for example maize starch, and lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The tablets and capsules may conveniently each contain 1 to 500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

Compositions of the invention suitable for rectal administration are the known pharmaceutical forms for such administration, for example suppositories with cocoa butter or polyethylene glycol bases.

Compositions of the invention suitable for parenteral administration are the known pharmaceutical forms for such administration, for example sterile suspensions in aqueous and oily media or sterile solutions in a suitable solvent.

Compositions for topical administration may comprise a matrix in which the pharmacologically active compounds of the present invention are dispersed so that the compounds are held in contact with the skin in order to administer the compounds transdermally. Alternatively the active compounds may be dispersed in a pharmaceutically acceptable cream or ointment base.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The pharmaceutical compositions containing a therapeutically effective amount of a compound of formula I may be used to treat depression in mammals including human beings. In such treatment the amount of the compound of formula I administered per day is in the range 1 to 1000 mg preferably 5 to 500 mg.

Compounds of formula I in which $R_4$ is CHO may be prepared by the reductive amidation of ketones of formula V

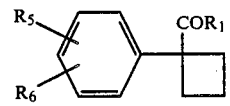

for example with formamide and formic acid or ammonium formate and formic acid to give compounds of formula I in which $R_4$ is CHO and $R_3$ is H or with formamides of formula $HCONHR_3$ in which $R_3$ is an alkyl or cycloalkyl group and formic acid or amines of formula $R_3NH_2$ in which $R_3$ is an alkyl or cycloalkyl group and formic acid.

Compounds of formula I in which $R_4$ is CHO may be prepared by the formylation of compounds of Formula I in which $R_4$ is H for example by reaction with methyl formate.

Compounds of formula I in which $R_3$ is other than H and $R_4$ is CHO may be prepared by reacting compounds of formula I in which $R_3$ is H and $R_4$ is CHO with a compound of formula $R_3X$ where X is a leaving group such as a halo group in the presence of a base.

Compounds of formula I may be prepared by the reductive amination of ketones of formula V.

Examples of suitable reductive amination processes are given below:

(a) for compounds of formula I in which $R_3$ and $R_4$ are H, by reaction of the ketone with an ammonium salt for example ammonium acetate and a reducing agent such as sodium cyanoborohydride, (b) for compounds of formula I in which $R_3$ is alkyl or cycloalkyl and $R_4$ is H by reaction of the ketone with an amine of formula $R_3NH_2$ and a reducing agent such as sodium cyanoborohydride or sodium borohydride, (c) for compounds of formula I in which neither $R_3$ nor $R_4$ is hydrogen or in which $R_3$ and $R_4$ together with the nitrogen atom form a heterocyclic ring, by reaction of the ketone with an amine of formula $HNR_3R_4$ and either formic acid or a reducing agent such as sodium cyanoborohydride, (d) for compounds of formula I in which one or both of $R_3$ and $R_4$ are H or an alkyl or a cycloalkyl group or in which $R_3$ and $R_4$ together with the nitrogen atom form a heterocyclic ring, by catalytic hydrogenation at elevated temperature and pressure of a mixture of the ketone and an amine of formula $HNR_3R_4$.

Compounds of formula I in which $R_3$ and $R_4$ are both alkyl groups may be prepared by reacting a ketone of formula V with a dialkyl formamide of formula $HCONR_3R_4$ for example in the presence of formic acid.

Compounds of formula I may be prepared by the reduction of compounds of formula VI

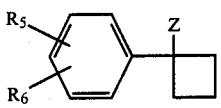

VI in which
(a) Z is a group of formula $-CR_1=NOH$ or an ester or ether thereof to give compounds of formula I in which $R_2$, $R_3$ and $R_4$ are H;
(b) Z is a group of formula $-CR_1=NR_3$ (where $R_3$ is other than H or CHO) to give compounds of formula I in which $R_2$ and $R_4$ are H;
(c) Z is a group of formula $-CR_1=NY$ in which Y represents a metal-containing moiety derived from an organometallic reagent to give compounds of formula I in which $R_2$, $R_3$ and $R_4$ are H;

Suitable reducing agents for the above reactions include sodium borohydride, sodium cyanoborohydride, or lithium aluminium hydride.

In (c) above Y is preferably MgBr derived from a Grignard reagent or Li derived from an organolithium compound.

Compounds of formula I may be prepared by the reaction of an organometallic reagent for example a Grignard reagent of formula $R_1MgX$ where X is Cl, Br or I or an organolithium compound of formula $R_1Li$ with an imine of formula VII

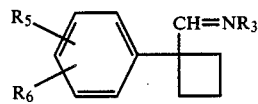

VII followed by hydrolysis to give a secondary amine of formula I.

Compounds of formula I in which $R_3$ and $R_4$ are H may be prepared by the decarboxylative rearrangement, for example using iodosobenzene-bistrifluoroacetate or by a Hofmann reaction using bromine in alkaline solution, of amides of formula VIII

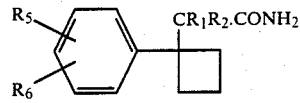

VIII

Compounds of formula I in which $R_3$ and $R_4$ are H may be prepared by the decarboxylative rearrangement of acyl azides in the Curtius reaction. The acyl azides may be formed for example by reaction of acid chlorides of formula IX with sodium azide.

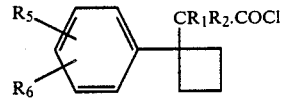

IX

Compounds of formula I in which $R_3$ and $R_4$ are H may be prepared by a Schmidt reaction in which carboxylic acids of formula X react with hydrazoic acid

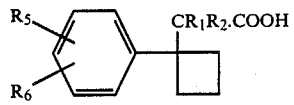

X

Compounds of formula I in which $R_4$ is H may be prepared by hydrolysis of compounds of formula I in which $R_4$ is CHO, for example by acid hydrolysis.

Compounds of formula I in which $R_4$ is methyl may be prepared by reduction of compounds of formula I in which $R_4$ is CHO, for example by lithium aluminium hydride or by sodium bis(2-methoxyethoxy)aluminium hydride.

Compounds of formula I in which one or both of $R_3$ and $R_4$ is other than H may be prepared from compounds of formula I in which one or both of $R_3$ and $R_4$ are hydrogen by methods which are well known in the art for the conversion of primary to secondary or tertiary amines or for the conversion of secondary to tertiary amines. The following are given as examples of suitable processes:

(a) by alkylating primary amines of formula I to give secondary amines of formula I for example by a process which includes the steps of protecting the primary amine with a protecting group such as trifluoroacetyl, alkylating with an alkyl halide and removing the protecting group for example by hydrolysis;

(b) by alkylating primary amines of formula I, for example, with an alkyl halide to give tertiary amines of formula I in which $R_3$ and $R_4$ are the same;

(c) by alkylating secondary amines of formula I, for example, with an alkyl halide to give tertiary amines of formula I in which $R_3$ and $R_4$ may be different;

(d) by reacting primary amines of formula I with sodium borohydride and acetic acid to give secondary amines of formula I in which $R_3$ is ethyl and $R_4$ is H;

(e) by reacting primary amines of formula I with formaldehyde and formic acid to give tertiary amines of formula I in which both $R_3$ and $R_4$ are methyl (f) by reacting secondary amines of formula I in which $R_4$ is H with formaldehyde and formic acid to give tertiary amines of formula I in which $R_4$ is methyl (g) by formylating primary amines of formula I, for example by reaction with methyl formate, and reducing the resulting formamides, for example with lithium aluminium hydride to give secondary amines of formula I in which $R_3$ is methyl and $R_4$ is H;

(h) by formylating secondary amines of formula I, for example by reaction with methyl formate, and reducing the resulting formamides, for example with lithium aluminium hydride to give tertiary amines of formula I in which $R_4$ is methyl.

(i) by acylating primary amines of formula I, for example by reaction with an acyl chloride of formula $R_{12}COCl$ or an anhydride of formula $(R_{12}CO)_2O$ in which $R_{12}$ is an alkyl, alkenyl or alkynyl group and reducing the resulting amides for example with lithium aluminium hydride to give secondary amines of formula I in which $R_3$ is —$CH_2R_{12}$ and $R_4$ is H.

(j) by acylating secondary amines of formula I in which $R_4$ is H for example by reaction with an acyl chloride of formula $R_{12}COCl$ or an anhydride of formula $(R_{12}CO)_2O$ in which $R_{12}$ is an alkyl, alkenyl or alkynyl group and reducing the resulting amides for example with lithium aluminium hydride to give tertiary amines in which $R_4$ is $CH_2R_{12}$;

(k) by reacting primary amines of formula I with an aldehyde of formula $R_{13}CHO$ in which $R_{13}$ may be an alkyl group, an alkenyl or alkynyl group or with a ketone of formula $R_{14}COR_{15}$ in which $R_{14}$ and $R_{15}$ which may be the same or different are an alkyl group, alkenyl group, alkynyl group or $R_{14}$ and $R_{15}$ together with carbon atom to which they are attached form an alicyclic ring and reducing the resulting imines or enamines for example with sodium cyanoborohydride or, when $R_{13}$, $R_{14}$ or $R_{15}$ are not alkenyl or alkynyl, by catalytic hydrogenation to give secondary amines of formula I in which $R_3$ is $R_{13}CH_2$— and

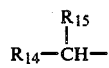

respectively;

(l) by reacting primary amines of formula I with a non-geminally disubstituted alkane containing 2 or 3 carbon atoms between the carbon atoms carrying the substituents which may be for example halo preferably bromo, or p-toluenesulphonyloxy to give compounds of formula I in which $R_3$ and $R_4$ together with the nitrogen to which they are attached fo a heterocyclic ring containing no heteroatoms other than the nitrogen atom.

The ketones of formula V may be prepared by the hydrolysis of imines of formula XI

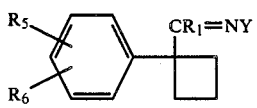

in which Y represents a metal-containing moiety derived from an organometallic reagent. The imines of formula XI may be prepared by the reaction of said organometallic reagent with a cyano compounds of formula XII

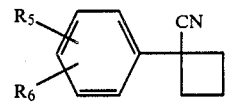

Suitable organometallic reagents include Grignard reagents of formula $R_1MgX$ where X is Cl, Br or I (Y=MgX) and organolithium compounds of formula $R_1Li$ (Y=Li).

Ketones of formula V may be prepared by the reaction of carboxylic acid derivatives such as amides or acid halides with an organometallic reagent for example by the reaction of an acid chlorides of formula XIII

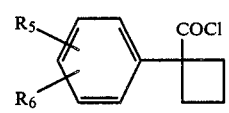

with a Grignard reagent of formula $R_1MgX$ where X is Cl, Br or I at low temperatures or by the reaction of carboxylic acids of formula XIV

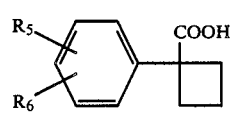

with an organometallic reagent, for example an organolithium compound of formula $R_1Li$.

Ketones of formula V in which $R_1$ is alkyl (e.g. methyl may be prepared by the reaction of a diazoalkane (e.g. diazomethane) with aldehydes of formula XV

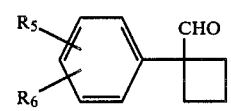

Compounds of formula VI in which Z is a group of formula —$CR_1$=NOH or ethers or esters thereof may be prepared by the reaction of hydroxylamine or an ether or ester thereof with ketones of formula V.

Compounds of formula VI in which Z is a group of formula —$CR_1$=$NR_3$ may be prepared by the reaction of amines of formula $R_3NH_2$ with ketones of formula V.

The preparation of compounds of formula VI in which Z is a group of formula —$CR_1$=NY has been described above in respect of compounds of formula XI.

Imines of formula VII may be prepared by reaction of amines of formula $R_3NH_2$ with aldehydes of formula XV.

Amides of formula VIII may be prepared by the reaction of ammonia with carboxylic acid derivatives for example acid chlorides of formula IX or they may be prepared from cyano compounds of formula XVI for example by hydration with aqueous acids or by reaction with hydrogen peroxide in the presence of a base.

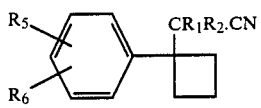

XVI

Carboxylic acids of formula X and XIV may be prepared by the hydrolysis, for example basic hydrolysis, of cyano compounds of formula XVI and XII respectively. Carboxylic acids of formula X may be prepared by the reaction of amides of formula VIII with nitrous acid. Carboxylic acids of formula XIV may be prepared by the reaction of nitrous acid with the amides formed by (a) the reaction of ammonia with carboxylic acid derivatives for example acid chlorides of formula XIII or (b) by the reaction of cyano compounds of formula XII with hydrogen peroxide in the presence of a base.

Cyano compounds of formula XII may be prepared by the reaction of cyano compounds of formula XVII

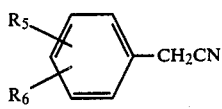

XVII with a 1,3-disubstituted propane for example 1,3-dibromopropane and a base such as sodium hydride.

Cyano compounds of formula XVIII

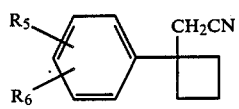

XVIII may be prepared from cyano compounds of formula XII by for example the following series of reactions
(a) hydrolysis of the cyano group to form a carboxylic acid of formula XIV;
(b) reduction of the carboxylic acid for example with lithium aluminium hydride or borane-dimethylsulphide complex to form the corresponding alcohol;
(c) replacement of the hydroxy group of the alcohol by a leaving group for example a p-toluene sulphonyloxy group and
(d) replacement of the leaving group with a cyano group. Cyano compounds of formula XVI in which one or both of $R_1$ and $R_2$ are other than H may be prepared from the corresponding cyano compounds of formula XVI in which $R_1$ and/or $R_2$ are H, for example by alkylation with an alkyl halide in the presence of a base such as lithium diisopropylamide.

Cyano compounds of formula XVI in which $R_2=H$ may also be prepared by reacting ketones of formula V with a reagent for introducing a cyano group such as p-toluenesulphonylmethyl isocyanide.

Acid chlorides of formula XIII and IX may be prepared by the reaction of carboxylic acids of formula XIV and X respectively with for example thionyl chloride.

Aldehydes of formula XV may be prepared by methods well known to those skilled in the art. The following are given as examples of suitable methods:
(a) by the reduction of cyano compounds of formula XII with for example di-tert-butylaluminium hydride or diisobutylaluminium hydride.

(b) by the reduction of carboxylic acid derivatives, for example
   (i) by the reduction of tertiary amides formed by the reaction of secondary amines with acid chlorides of formula XIII for example when the secondary amine is a dialkylamine using lithium diethoxyaluminohydride as reducing agent or when the secondary amine is ethyleneimine using lithium aluminium hydride as the reducing agent,
   (ii) by the reaction of acid chlorides of formula XIII for example with lithium tri-tert butoxyaluminohydride.
(c) by the oxidation of alcohols (prepared by the reduction of carboxylic acids of formula XIV) with, for example, chromium trioxide-pyridine complex in dichloromethane under anhydrous conditions.

Ketones of formula V (except those in which $R_5$ and $R_6$ are H and $R_1$ is methyl or ethyl), the compounds of formula VI (except those in which Z is $CR_1=NY$ and $R_5$ and $R_6$ are H and $R_1$ is methyl and ethyl), the imines of formula VII (except those in which $R_5$ and $R_6$ are H), and XI (except those in which $R_5$ and $R_6$ are H and $R_1$ is methyl or ethyl), the amides of formula VIII, the carboxylic acids of formula X (except those in which $R_1$, $R_2$, $R_5$ and $R_6$ are H), the cyano compounds of formula XVI and the acid chlorides of formula IX (except those in which $R_1$, $R_2$, $R_5$ and $R_6$ are H) which are described herein as intermediates are novel compounds. Some of the cyano compounds of formula XII and XVII are novel compounds. Such novel compounds form a further aspect of the present invention.

Novel formamides of formula XIX

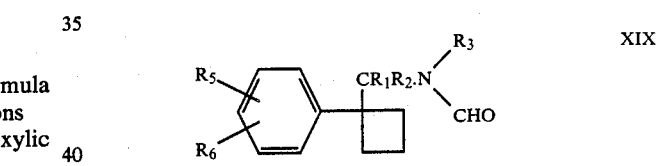

XIX are described herein as intermediates, in the preparation of compounds of formula I and such novel formamides form a further aspect of the present invention.

The therapeutic activity of the compounds of formula I has been indicated by assessing the ability of the compounds to reverse the hypothermic effects of reserpine in the following manner. Male mice of the Charles River CD1 strain weighing between 18 and 30 grammes were separated into groups of five and were supplied with food and water ad libitum. After five hours the body temperature of each mouse was taken orally and the mice were injected intraperitoneally with reserpine (5 mg/kg) in solution in deionised water containing ascorbic acid (50 mg/ml). The amount of liquid injected was 10 ml/kg of body weight. Nine hours after the start of the test food was withdrawn but water was still available ad libitum. Twenty-four hours after the start of the test the temperatures of the mice were taken and the mice were given the test compound suspended in a 0.25% solution of hydroxy ethyl cellulose (sold under the trade name Cellosize QP 15000 by Union Carbide) in deionised water at a dose volume of 10 ml/kg of body weight. Three hours later the temperatures of all the mice were again taken. The percentage reversal of the reserpine-induced loss of body temperature is then calculated by the formula:

$$\frac{\text{(Temperature after 27 hrs} - \text{Temperature after 24 hours)}}{\text{(Temperature after 5 hrs} - \text{Temperature after 24 hours)}} \times 100$$

The mean value for each group of five mice was taken at several dose rates to enable a value of the mean dose which causes a 50% reversal (ED50) to be obtained. All the compounds which are the final products of the Examples hereinafter gave values of ED50 of 30 mg/kg or less. It is widely understood by those skilled in the art that this test is indicative of compounds having antidepressant activity in humans.

Table I lists compounds of formula I which gave a value of ED50 in the above test of 10 mg/kg or less.

Table I

1-[1-(3,4-dichlorophenyl)cyclobutyl]ethylamine hydrochloride
N-methyl-1-[1-(3,4-dichlorophenyl)cyclobutyl]ethylamine hydrochloride
N,N-dimethyl-1-[1-(3,4-dichlorophenyl)cyclobutyl]ethylamine hydrochloride
1-[1-(4-iodophenyl)cyclobutyl]ethylamine hydrochloride
N-methyl-1-[1-(4-iodophenyl)cyclobutyl]ethylamine hydrochloride
N,N-dimethyl-1-[1-(4-iodophenyl)cyclobutyl]ethylamine hydrochloride
N-methyl-1-[1-(2-naphthyl)cyclobutyl]ethylamine hydrochloride
N,N-dimethyl-1-[1-(4-chloro-3-trifluoromethylphenyl)cyclobutyl]ethylamine hydrochloride
1-[1-(4-chlorophenyl)cyclobutyl]butylamine hydrochloride
N-methyl-1-[1-(4-chlorophenyl)cyclobutyl]butylamine hydrochloride
N,N-dimethyl-1-[1-(4-chlorophenyl)cyclobutyl]butylamine hydrochloride
1-[1-(3,4-dichlorophenyl)cyclobutyl]butylamine hydrochloride
N-methyl-1-[1-(3,4-dichlorophenyl)cyclobutyl]butylamine hydrochloride
N,N-dimethyl-1-[1-(3,4-dichlorophenyl)cyclobutyl]butylamine hydrochloride
1-[1-(4-biphenylyl)cyclobutyl]butylamine hydrochloride
N,N-dimethyl-1-[1-(4-biphenylyl)cyclobutyl]butylamine hydrochloride
1-[1-(4-chloro-3-fluorophenyl)cyclobutyl]butylamine hydrochloride
N-formyl-1-[1-(4-chloro-3-fluorophenyl)cyclobutyl]butylamine
1-[1-(3-chloro-4-methylphenyl)cyclobutyl]butylamine hydrochloride
N-formyl-1-[1-phenylcyclobutyl]butylamine
1-[1-(3-trifluoromethylphenyl)cyclobutyl]butylamine hydrochloride
1-[1-(naphth-2-yl)cyclobutyl]butylamine hydrochloride
1-[1-(6-chloronaphth-2-yl)cyclobutyl]butylamine
N-methyl-1-[1-(4-chlorophenyl)cyclobutyl]-2-methylpropylamine hydrochloride
1-[1-(4-chlorophenyl)cyclobutyl]pentylamine hydrochloride
N-methyl-1-[1-(4-chlorophenyl)cyclobutyl]pentylamine hydrochloride
N,N-dimethyl-1-[1-phenylcyclobutyl]-3-methylbutylamine hydrochloride
1-[1-(4-chlorophenyl)cyclobutyl]-3-methylbutylamine hydrochloride
N-methyl-1-[1-(4-chlorophenyl)cyclobutyl]-3-methylbutylamine hydrochloride
N,N-dimethyl-1-[1-(4-chlorophenyl)cyclobutyl]-3-methylbutylamine hydrochloride
N-formyl-1-[1-(4-chlorophenyl)cyclobutyl]-3-methylbutylamine
N,N-dimethyl-1-[1-(3,4-dichlorophenyl)cyclobutyl]-3-methylbutylamine hydrochloride
N-methyl-1-[1-(naphth-2-yl)cyclobutyl]-3-methylbutylamine hydrochloride
N-methyl-1-[1-(3,4-dimethylphenyl)cyclobutyl]-3-methylbutylamine hydrochloride
[1-(4-chlorophenyl)cyclobutyl](cyclopropyl)methylamine hydrochloride
N-methyl-[1-(4-chlorophenyl)cyclobutyl](cyclopentyl)methylamine hydrochloride
[1-(4-chlorophenyl)cyclobutyl](cyclohexyl)methylamine hydrochloride
N-methyl-[1-(4-chlorophenyl)cyclobutyl](cyclohexyl)methylamine hydrochloride
[1-(3,4-dichlorophenyl)cyclobutyl](cyclohexyl)methylamine hydrochloride
N-methyl-[1-(3,4-dichlorophenyl)cyclobutyl](cyclohexyl)methylamine hydrochloride
[1-(4-chlorophenyl)cyclobutyl](cycloheptyl)methylamine hydrochloride
1-[1-(4-chlorophenyl)cyclobutyl]-2-cyclopropylethylamine hydrochloride
N,N-dimethyl-1-[1-(4-chlorophenyl)cyclobutyl]-2-cyclohexylethylamine hydrochloride
α-[1-(4-chlorophenyl)cyclobutyl]benzylamine hydrochloride
N-methyl-α-[1-(4-chlorophenyl)cyclobutyl]benzylamine hydrochloride
1-[1-(4-chloro-2-fluorophenyl)cyclobutyl]butylamine
N,N-dimethyl-1-[1-(4-chloro-2-fluorophenyl)cyclobutyl]butylamine hydrochloride
N-ethyl-1-[1-(3,4-dichlorophenyl)cyclobutyl]ethylamine hydrochloride
N,N-diethyl-1-[1-(3,4-dichlorophenyl)cyclobutyl]ethylamine hydrochloride The invention will now be illustrated by the following Examples which are given by way of example only. All compounds were characterised by conventional analytical techniques and gave satisfactory elemental analyses. All melting and boiling points are expressed in degrees Celsius.

EXAMPLE 1

A solution of 3,4-dichlorobenzyl cyanide (25 g) and 1,3-dibromopropane (15 ml) in dry dimethyl sulphoxide (150 ml) was added dropwise under nitrogen to a stirred mixture of sodium hydride (7.5 g) dispersed in mineral oil (7.5 g) and dimethylsulphoxide (200 ml) at a temperature in the range 30° to 35° C. The mixture was stirred at room temperature for two hours and propan-2-ol (8 ml) and then water (110 ml) were added dropwise. The mixture was filtered through a diatomaceous earth sold under the Registered Trade Mark CELITE and the solid residue washed with ether. The ether layer was separated, washed with water, dried and evaporated. 1-(3,4-Dichlorophenyl)-1-cyclobutanecarbonitrile (b.p. 108°–120° C. at 0.15 Hg) was isolated by distillation. This method is a modification of that described by Butler and Pollatz (J. Org. Chem., Vol. 36, No. 9, 1971, p. 1308).

The 1-(3,4-dichlorophenyl)-1-cyclobutanecarbonitrile prepared as above (21.7 g) was dissolved in dry ether (50 ml) and the solution was added under nitrogen to the product of the reaction of gaseous methyl bromide with magnesium turnings (3.9 g) in dry ether (150 ml). The mixture was stirred at room temperature for two hours and then under reflux for two hours. Crushed ice and then concentrated hydrochloric acid (100 ml) were added and the mixture heated under reflux for two hours. The ether layer was separated, washed with water and aqueous sodium bicarbonate, dried and evaporated. 1-Acetyl-1-(3,4-dichlorophenyl)cyclobutane (b.p. 108°–110° at 0.2 mm Hg) was isolated by distillation.

1-Acetyl-1-(3,4-dichlorophenyl)cyclobutane (9.1 g) prepared as above, formamide (6.5 ml) and 98% formic acid (3 ml) were heated at 180° C. for sixteen hours to give N-formyl-1-[1-(3,4-dichlorophenyl)cyclobutyl]ethylamine. Concentrated hydrochloric acid (20 ml) was added and the mixture heated under reflux for three hours. The solution was then cooled, washed with ether and sodium hydroxide solution added. The product was extracted with ether, and the ether extract washed with water, dried and evaporated. 1-[1-(3,4-Dichlorophenyl)cyclobutyl]ethylamine (b.p. 112°–118° at 0.2 mm Hg) was isolated by distillation. The amine was dissolved in propan-2-ol and concentrated hydrochloric acid and the solution evaporated to dryness to give 1-[1-(3,4-dichlorophenyl)cyclobutyl]ethylamine hydrochloride (m.p. 185°–195° C.). (Formula I $R_1$=Me; $R_2$,$R_3$ and $R_4$=H; $R_5$=4—Cl; $R_6$=3—Cl).

EXAMPLE 1a

The preparation of N-formyl-1-[1-(3,4-dichlorophenyl)cyclobutyl]ethylamine (m.p. 124°–125° C.) (Example 1(a) Formula I $R_1$=Me; $R_2$=H; $R_3$=H; $R_4$=CHO; $R_5$=4—Cl and $R_6$=3—Cl) described above was repeated and the product isolated by cooling the reaction mixture and collecting the solid produced by filtration. The formamide was then hydrolysed by concentrated hydrochloric acid in industrial methylated spirit to give the hydrochloride salt of 1-[1-(3,4-dichlorophenyl)cyclobutyl]ethylamine.

In a similar manner to that described above in Example Ia in the following compounds were prepared. The conditions for the hydrolysis of the formamides which were isolated by appropriate methods are shown in the footnotes.

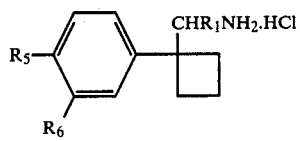

| Example | $R_1$ | $R_5$ | $R_6$ | b.p. (free base) | m.p. of HCl salt | Note |
|---|---|---|---|---|---|---|
| 1(b) | methyl | Cl | H | 107°/1.2 mm Hg | | A |
| 1(c) | n-butyl | Cl | H | | 138–139° | B |
| 1(d) | methyl | I | H | | 205–207° | C |
| 1(e) | methyl | Cl | $CF_3$ | | 216–217° | D |

A aqueous HCl/industrial methylated spirit
B The 1-valeryl-1-(4-chlorophenyl)cyclobutane was prepared in tetrahydrofuran. Hydrolysis was performed using concentrated HCl/industrial methylated spirit.
C concentrated HCl/diethyleneglycoldimethyl ether (in a similar manner to that described later in Example 12).
D concentrated HCl/industrial methylated spirit.

EXAMPLE 2

The product of Example 1 (4.04 g), water (0.5 ml) and 98% formic acid (3.6 ml) were mixed with cooling. 37–40% Aqueous formaldehyde (3.8 ml) was added and the solution was heated at 85°–95° C. for five hours. The solution was evaporated to dryness and the residue acidified with concentrated hydrochloric acid and the water removed by repeated addition of propan-2-ol followed by evaporation in vacuo. Crystals of N,N-dimethyl-1-[1-(3,4-dichlorophenyl)cyclobutyl]ethylamine hydrochloride (m.p. 211°–213° C.) (Formula I $R_1$=Me; $R_2$=H; $R_3$,$R_4$=Me; $R_5$=4—Cl; $R_6$=3—Cl) were isolated.

In a similar way to that described above the compounds of Example 1(b) and 1(d) were converted into the compounds listed below.

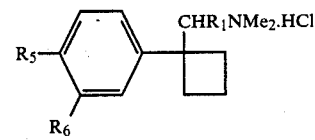

| Example | Starting Material | $R_1$ | $R_5$ | $R_6$ | m.p. of HCl salt | b.p. of free base |
|---|---|---|---|---|---|---|
| 2(a) | 1(b) | methyl | Cl | H | | 98–100°/0.5 mm |
| 2(b) | 1(d) | methyl | I | H | 260–261° | |

EXAMPLE 3

In a similar manner to that described above in Examples 1 and 2 N,N-dimethyl-1-[1-(4-biphenylyl)cyclobutyl]ethylamine hydrochloride (m.p. 196°–197° C.) was prepared. (Formula I $R_1$=Me; $R_2$=H; $R_3$,$R_4$=Me; $R_5$=4-phenyl and $R_6$=H).

EXAMPLE 4

1-Acetyl-1-(3,4-dichlorophenyl)cyclobutane (15 g) prepared as described in Example 1, N-methylformamide (47.5 ml) 98% formic acid (10.3 ml) and a 25% aqueous solution of methylamine (1.5 ml) were mixed and heated with stirring at 170°–180° for eight hours. The mixture was cooled and extracted with ether. The ether extract was washed, dried and evaporated to yield a light yellow oil which was heated under reflux with concentrated hydrochloric acid (50 ml) for two hours. Industrial methylated spirit (IMS) (50 ml) was added and the mixture heated under reflux for sixteen hours. The mixture was then cooled to 0° C. and the white precipitate collected by filtration, washed with acetone and dried. The product, N-methyl-1-[1-(3,4-dichlorophenyl)cyclobutyl]ethylamine hydrochloride, had a melting point of 254° to 256° C. (Formula I $R_1$=Me; $R_2$=H; $R_3$=Me; $R_4$=H; $R_5$=4—Cl and $R_6$=3—Cl).

In a similar manner to that described above the following compounds of formula I were prepared

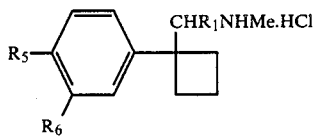

| Example | R$_1$ | R$_5$ | R$_6$ | b.p. of amine | m.p. of HCl salt | Note |
|---|---|---|---|---|---|---|
| 4(a) | Me | Cl | H | 98–100°/0.15 mm | 240–241° | |
| 4(b) | Me | H | Cl | | 269–272° | |
| 4(c) | Me | Br | H | 96–98°/0.1 mm | 251–255° | |
| 4(d) | Me | H | Br | | 251–255° | |
| 4(e) | Me | CF$_3$ | H | | 219–221° | |
| 4(f) | Me | H | CF$_3$ | | 225–228° | |
| 4(g) | Me | —(CH=CH)$_2$— | | | 254–257° | |
| 4(h) | Me | Cl | CF$_3$ | | 198–200° | |
| 4(i) | Et | Cl | H | | 238–240° | |
| 4(j) | Pr | Cl | H | | 228–229° | A |
| 4(k) | Bu | Cl | H | | 152–153° | A |
| 4(l) | Me | I | H | | 242–243° | |

Note A
The starting ketone was prepared in tetrahydrofuran as reaction solvent in place of ether.

EXAMPLE 5

A mixture of 70% aqueous ethylamine (50 ml) and water (100 ml) was gradually mixed with a mixture of 98% formic acid (50 ml) and water (100 ml) to give a neutral solution which was evaporated at 100° C./100 mm Hg until 180 ml of water had been collected. The residue was heated to 140° C. and 1-acetyl-1-(4-chlorophenyl)cyclobutane (10.4 g) prepared in a similar manner to that described in Example 1 for 1-acetyl-1-(3,4-dichlorophenyl)cyclobutane and 98% formic acid (10 ml) were added. The mixture was heated on an oil bath at a temperature of 180°–200° C. for sixteen hours. The mixture was distilled until an internal temperature of 170° C. was obtained and this temperature was maintained for two hours. Any volatile material was removed by distillation at 160° C./20 mm and the residue heated under reflux with concentrated hydrochloric acid (15 ml) and industrial methylated spirit (IMS) (15 ml) for three hours. The IMS was evaporated on a rotary evaporator and the residue washed with ether. The aqueous phase was brought to pH 12 with sodium hydroxide and extracted with ether. The ether extract was dried and on evaporation yielded a residue which was treated with aqueous hydrochloric acid to give N-ethyl-1-[1-(4-chlorophenyl)cyclobutyl]ethylamine hydrochloride (m.p. 203°–205° C.) (Formula I (R$_1$=Me; R$_2$=H; R$_3$=Et; R$_4$=H; R$_5$=4—Cl; R$_6$=H).

EXAMPLE 6

1-(4-Chlorophenyl)-1-cyclobutanecarbonitrile (15 g) prepared in a similar manner to the 1-(3,4-dichlorophenyl)cyclobutanecarbonitrile of Example 1 in dry ether (50 ml) was added to the product of the reaction between magnesium turnings (3.18 g) and propyl bromide (15.99 g) in dry ether (50 ml). The ether was replaced by tetrahydrofuran and the mixture heated with stirring under reflux for eighteen hours. The mixture was cooled and ice and then concentrated hydrochloric acid (52 ml) added. The resulting mixture was stirred under reflux for ten hours and extracted with ether. The ether extract yielded a residue from which 1-butyryl-1-(4-chlorophenyl)cyclobutane (b.p. 106°–108°/0.3 mm Hg) was distilled.

A mixture of the ketone produced as described above (21 g) and 98% formic acid (6 ml) was added over a period of one and a half hours to formamide (15 ml) at 160° C. After completion of the addition the temperature was raised to 180° to 185° C. and maintained in this range for five hours. The mixture was cooled and extracted with chloroform to yield a thick gum which on heating with petroleum ether (b.p. 60°–80°) gave a colourless solid which was recrystallised from petroleum ether (b.p. 60°–80°) to yield N-formyl-1-[1-(4-chlorophenyl)cyclobutyl]butylamine (m.p. 97.5 to 98.5° C.) (Formula I (R$_1$=propyl; R$_2$=H; R$_3$=H; R$_4$=CHO; R$_5$=4-Cl; R$_6$=H).

EXAMPLE 7

A solution of 1-(3,4-dichlorophenyl)-1-cyclobutanecarbonitrile prepared as described in Example 1 (35.2 g) in ether (100 ml) was added to a solution of propyl magnesium bromide prepared by the reaction of propyl bromide (32 g) with magnesium turnings (6.36 g) in ether (100 ml). The ether was replaced by dry toluene and the mixture heated under reflux for one hour. Water (200 ml) and then concentrated hydrochloric acid (120 ml) were added and the mixture heated under reflux for one hour. The reaction mixture was extracted with ether and after washing and drying the extract yielded a residue from which 1-butyryl-1-(3,4-dichlorophenyl)cyclobutane (b.p. 120°–128° C. at 0.25 mm) was distilled.

The ketone produced as described above (37.0 g) and 98% formic acid (9 ml) were added to formamide (23.5 ml) at 170° C. and the temperature kept at 175°–180° C. for five hours. A further portion of formic acid (4.5 ml) was added and the mixture was maintained at 175°–180° C. for a further fifteen hours. The mixture was extracted with ether which on evaporation gave a thick oil which was crystallised from petroleum ether (b.p. 60°–80°) to give N-formyl-1-[1-(3,4-dichlorophenyl)cyclobutyl]butylamine having a melting point of 103°–105° C. (Formula I R$_1$=propyl; R$_2$=H; R$_3$=H; R$_4$=CHO; R$_5$=4—Cl and R$_6$=3—Cl).

In a similar manner to that described above the following compounds were made

| Example | R$_1$ | R$_5$ | R$_6$ | m.p. (°C.) |
|---|---|---|---|---|
| 7(a) | isobutyl | Cl | H | 110–112° |
| 7(b) | propyl | Cl | F | 115–116° |
| 7(c) | phenyl | Cl | H | 94–96° |
| 7(d) | propyl | H | H | 98–102° |

EXAMPLE 8

The product of Example 7 (4.0 g) in dry tetrahydrofuran (25 ml) was added rapidly to a stirred mixture of lithium aluminium hydride (1.4 g) in dry tetrahydrofuran (25 ml) under nitrogen. The mixture was heated under reflux for five hours and then cooled. Water (15 ml) and then 10% sodium hydroxide solution (3 ml) were added and the mixture filtered through diatomaceous earth sold under the Registered Trade Mark CELITE. The product was extracted into ether, back extracted into 5N hydrochloric acid and the aqueous layer was basified and extracted with ether. The ether extract yielded an oil which was dissolved in propan-2-ol (5 ml) and concentrated hydrochloric acid was added to pH 2. Evaporation of the resulting solution gave a white solid which was collected, washed with acetone and dried. The product was N-methyl-1-[1-(3,4-dichlorophenyl)cyclobutyl]butylamine hydrochloride and had a melting point of 234°–235° C. (Formula I $R_1$=propyl; $R_2$=H; $R_3$=H; $R_4$=Me; $R_5$=4—Cl and $R_6$=3—Cl)

In a similar manner to that described above the following compounds were prepared

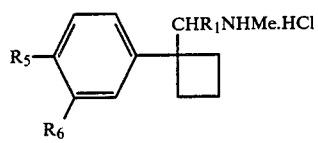

| Example | $R_1$ | $R_5$ | $R_6$ | m.p. (°C.) |
|---|---|---|---|---|
| 8(a) | phenyl | Cl | H | 275–278° |
| 8(b) | propyl | Cl | H | 223–228° |

EXAMPLE 9

The product of Example 7 (10 g) in solution in ether (50 ml) was added to a 70% toluene solution of sodium bis(2-methoxyethoxy)aluminium hydride sold under the trade mark Red-al (40 ml) at a temperature in the range 25° to 30° C. The mixture was stirred at this temperature for four hours. Water (25 ml) was added dropwise with cooling and the mixture filtered through diatomaceous earth (CELITE). Aqueous NaOH was added and an ether extraction performed. The ether extract was washed with water and back extracted with 5N hydrochloric acid. A white solid (m.p. 232°–235 C.) appeared at the interface which was collected. Base was added to the aqueous phase and a further ether extraction performed. Evaporation of the ether extract yielded an oil which was dissolved in propan-2-ol (5 ml) and concentrated hydrochloric acid added to pH 2. Evaporation to dryness gave a white solid (m.p. 233°–236° C.). The white solids were combined and recrystallised from propan-2-ol to yield N-methyl-1-[1-(3,4-dichlorophenyl)cyclobutyl]butylamine hydrochloride (m.p. 236°–237° C.) (Formula I $R_1$=propyl; $R_2$=H; $R_3$=H; $R_4$=Me; $R_5$=4—Cl and $R_6$=3—Cl).

In a similar manner to that described above the following compounds were prepared. Where the formyl starting material was insoluble in ether, a solution of the reducing agent was added to a stirred suspension of the formyl compound. As the size of the group $R_1$ is increased the hydrochloride salts of the desired compounds become less soluble in the aqueous phase and more soluble in the organic phase so that appropriate modifications in the isolation procedure are required as will be apparent to those skilled in the art.

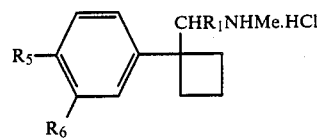

| Example | $R_1$ | $R_5$ | $R_6$ | m.p. |
|---|---|---|---|---|
| 9(a) | isopropyl | Cl | H | 257–259° |
| 9(b) | sec-butyl | Cl | H | 209–212° |
| 9(c) | isobutyl | Cl | H | 225–233° |
| 9(d) | cyclopentyl | Cl | H | 252–256° |
| 9(e) | n-hexyl | Cl | H | 117–118° |
| 9(f) | 4-methoxyphenyl | Cl | H | 264–266° |
| 9(g) | 3-methoxyphenyl | Cl | H | 254–255° |
| 9(h) | 2-methoxyphenyl | Cl | H | 149–153° |
| 9(i) | cyclohexyl | Cl | H | 170–172° |
| 9(j) | isobutyl | —(CH=CH)$_2$— | | 256–259° |
| 9(k) | cyclohexyl | Cl | Cl | 223–224° |
| 9(l) | isobutyl | Me | Me | (1) |
| 9(m) | propyl | OMe | H | 173–175° |
| 9(n) | methyl | phenyl | H | 116–118° |

(1) Boiling point of free base >150° at 1.0 mm Hg.

The product of Example 7 (4 g), diethyleneglycoldimethyl ether (25 ml), water (10 ml) and concentrated hydrochloric acid (10 ml) were mixed and heated under reflux for nine hours. The solution was washed with ether and aqueous NaOH added before an ether extraction was performed. The ether extract was washed with brine and water and yielded an oil on evaporation. The oil (3.19 g) was dissolved in a mixture of propan-2-ol (4 ml) and ether (20 ml) and concentrated hydrochloric acid (1.5 ml) added. The solvent was evaporated in vacuo. Repeated dissolution in industrial methylated spirit and evaporation in vacuo gave a gum which solidified on warming in vacuo. The product was recrystallised from petroleum ether (b.p. 100°–120° C.) and had a melting point of 201°–203° C. The product was 1-[1-(3,4-dichlorophenyl)cyclobutyl]butylamine hydrochloride (Formula I $R_1$=propyl; $R_2$=H; $R_3$, $R_4$=H; $R_5$=4—Cl and $R_6$=3—Cl).

In a similar manner to that described above the following compounds were prepared. As the size of the group $R_1$ is increased the hydrochloride salts of the desired compounds become less soluble in the aqueous phase and more soluble in the organic phase so that appropriate modifications in the isolation procedure are required as will be apparent to those skilled in the art.

| Example | $R_1$ | $R_5$ | $R_6$ | m.p. |
|---|---|---|---|---|
| 10(a) | isopropyl | Cl | H | 200–202° |
| 10(b) | sec-butyl | Cl | H | 178–179° |
| 10(c) | isobutyl | Cl | H | 163–165° |
| 10(d) | cyclopentyl | Cl | H | 185–210° (dec) |
| 10(e) | phenyl | Cl | H | 271–276° |
| 10(f) | 4-methoxyphenyl | Cl | H | 214–219° |
| 10(g) | cyclohexyl | Cl | H | 206–210° |
| 10(h) | isobutyl | H | H | 210–212° |
| 10(i) | cyclopropyl | Cl | H | 204–206° |
| 10(j) | propyl | Ph | H | 235–236° |
| 10(k) | propyl | Me | Cl | 214–217° |

-continued

Structure: R5-, R6- substituted phenyl with cyclobutyl bearing CHR1NH2·HCl

| Example | R1 | R5 | R6 | m.p. |
|---|---|---|---|---|
| 10(l) | propyl | —(CH=CH)2— | | 157–159° |
| 10(m) | cycloheptyl | Cl | H | 156–162° |
| 10(n) | cyclohexyl | Cl | Cl | 215° |
| 10(p) | methyl | Cl | F | 215–217° |
| 10(q) | propyl | OMe | H | 178–179° |
| 10(r) | propyl | Cl | F | 186–188° |
| 10(s) | propyl | Cl | H | 174–175° |
| 10(t) | cyclohexyl-methyl | Cl | H | 148–150° |
| 10(u) | cyclopropylmethyl | Cl | H | 184–185° |
| 10(v) | propyl | —CH=CH—CCl=CH— | | (a) |
| 10(w) | propyl | H | CF3 | 126–128° |
| 10(x) | 4-fluorophenyl | Cl | H | 279° |
| 10(y) (b) | methyl | —C=C—CH=CH— / CH  CH \\ CH—CH | | 248–262° |

(a) boiling point of free base 168° C./0.05 mm Hg.
(b) diethyleneglycoldimethyl ether replaced by ethyleneglycoldimethyl ether.

In a similar manner to that described above, 1-[1-(4-chloro-2-fluorophenyl)cyclobutyl]butylamine (b.p. 99° C./0.05 mm). (Formula I $R_1$=propyl; $R_2$, $R_3$ and $R_4$=H; $R_5$=4—Cl; $R_6$=2—F), 1-[1-(2-fluorophenyl)cyclobutyl]butylamine hydrochloride (m.p. 175°–177° C.). (Formula I $R_1$=propyl; $R_2$, $R_3$, $R_4$, $R_5$=H and $R_6$=2—F) and 1-[1-(4-chloro-2-methyl)cyclobutyl]butylamine hydrochloride (m.p. 188°–190° C.) (Formula I $R_1$=propyl; $R_2$, $R_3$ and $R_4$=H; $R_5$=4—Cl and $R_6$=2—Me) were prepared as Examples 10(z), 10(aa) and 10(bb) respectively.

EXAMPLE 11

The product of Example 10(c) (3.3 g) in the form of the free base, formic acid (2.99 g) and water (1 ml) were mixed with cooling. 37–40% Aqueous formaldehyde (3.93 ml) was added and the mixture heated for eighteen hours at a temperature of 85°–95° C. Excess dilute hydrochloric acid was added and the solution evaporated to dryness. The residue was basified with 5N sodium hydroxide solution and the product was extracted into ether. Evaporation of the ether yielded a pale yellow oil which was dissolved in a mixture of propan-2-ol (4 ml) and ether (20 ml) and concentrated hydrochloric acid (2 ml) was added dropwise. The solution was evaporated and the residue dissolved repeatedly in ethanol and evaporated in vacuo to give a gum which was triturated with petroleum ether (b.p. 60°–80°) to yield a yellow solid which was recrystallised from acetone. The product was N,N-dimethyl-1-[1-(4-chlorophenyl)cyclobutyl]-3-methylbutylamine hydrochloride (m.p. 195°–197° C.). (Formula I $R_1$=isobutyl; $R_2$=H; $R_3$, $R_4$=Me; $R_5$=4—Cl; $R_6$=H).

In a similar manner to that described above the following compounds of Formula I were prepared Structure: R5-, R6- substituted phenyl with cyclobutyl bearing CHR1NMe2·HCl

| Example | Starting Material | R1 | R5 | R6 | m.p. |
|---|---|---|---|---|---|
| 11(a) | 10(h) | isobutyl | H | H | 195–198° |
| 11(b) | 10(j) | propyl | Ph | H | 194–196° |
| 11(c) | 10(n) | cyclohexyl | Cl | Cl | 227–228° |
| 11(d) | 10(q) | propyl | OMe | H | 187–188° |
| 11(e) | 10(s) | propyl | Cl | H | 194–196° |
| 11(f) | 10(t) | cyclohexyl methyl | Cl | H | 194–196° |
| 11(g) | 10(u) | cyclopropylmethyl | Cl | H | 165–167° |
| 11(h) | 10(v) | propyl | —CH=CH—CCl=CH— | | (a) |
| 11(i) | — | isobutyl | Cl | Cl | 225–226° |
| 11(j) | 10(x) | 4-fluorophenyl | Cl | H | 234° |
| 11(k) | — | propyl | isopropyl | H | 211–213° |

(a) boiling point of free base <250° C./0.05 mm Hg.

EXAMPLE 11(l)

In a similar manner to that described above N,N-dimethyl-1-[1-(4-chloro-2-fluorophenyl)cyclobutyl]butylamine hydrochloride (m.p. 183°) was prepared. (Formula I $R_1$=propyl; $R_2$=H; $R_3$, $R_4$=Me; $R_5$=4—Cl; $R_6$=2—F)

EXAMPLE 12

The product of Example 7 (8.3 g), diethyleneglycoldimethyl ether (50 ml), water (20 ml) and concentrated hydrochloric acid (20 ml) were mixed and heated under reflux for sixteen hours. The mixture was poured into water, aqueous NaOH was added and the product extracted into ether. Evaporation gave a dark oil. A sample of this oil (7.9 g) water (0.7 ml) and formic acid (6.5 ml) were mixed and formaldehyde (6.5 ml) added. The mixture was heated under reflux for three hours and then concentrated hydrochloric acid (10 ml) and propan-2-ol (10 ml) were added. Evaporation to dryness gave N,N-dimethyl-1-[1-(3,4-dichlorophenyl)cyclobutyl]butylamine hydrochloride (m.p. 195°–196°) as a white solid (Formula I $R_1$=propyl; $R_2$=H; $R_3$, $R_4$=Me; $R_5$=4—Cl and $R_6$=3—Cl).

EXAMPLE 13

1-(4-Chlorophenyl)-1-cyclobutanecarbonitrile (37.6 g) prepared in a similar manner to the 1-(3,4-dichlorophenyl)-1-cyclobutanecarbonitrile described in Example 1 was added to a solution of potassium hydroxide (32.4 g) in diethyleneglycol (370 ml) and the mixture heated under reflux for three and a half hours. The reaction mixture was poured into an ice/water mixture and the resulting solution was washed with ether. The aqueous layer was added to a mixture of concentrated hydrochloric acid (100 ml) and ice and the resulting precipitate of 1-(4-chlorophenyl)-1-cyclobutanecarboxylic acid (m.p. 86°-88°) collected, washed with water and dried.

A solution of the acid (10.5 g) prepared as above in tetrahydrofuran (150 ml) was added dropwise under nitrogen to a stirred suspension of lithium aluminum hydride (2 g) in tetrahydrofuran (150 ml). The mixture was stirred under reflux for two hours and water added. The mixture was filtered through diatomaceous earth (CELITE—RTM) and the product extracted into ether. After washing with water and drying, the ether was evaporated to give a residue which was recrystallised from petroleum ether (b.p. 60°-80°). The product was 1-[1-(4-chlorophenyl)cyclobutyl]methyl alcohol (m.p. 60°-62° C.).

A solution of the alcohol prepared as described above (60 g) in pyridine (52 ml) was added dropwise to a solution of p-toluenesulphonylchloride (60 g) in pyridine (100 ml) cooled in ice. The temperature was allowed to rise to room temperature and remain there for eighteen hours. 1-[1-(4-Chlorophenyl)cyclobutyl]methyl p-toluene sulphonate (m.p. 99°-100° C.) was precipitated by pouring the reaction mixture into a mixture of ice and concentrated hydrochloric acid (200 ml).

A solution of the sulphonate compound (97 g) prepared as described above and sodium cyanide (16.6 g) in dimethyl sulphoxide (370 ml) was heated on a steam bath for eighteen hours. The mixture was poured into water and extracted with ether. After washing and drying the ether was evaporated to leave a solid residue of 2-[1-(4-chlorophenyl)cyclobutyl]acetonitrile (m.p. 63°-65° C.).

A solution of di-isopropylamine (16.5 g) in dry tetrahydrofuran (50 ml) was stirred under nitrogen at a temperature of 0° C. and a 1.6 M solution of n-butyllithium in hexane (100 ml) added dropwise. The reaction mixture was stirred for 30 minutes and then cooled to −78° C. A solution of 2-[1-(4-chlorophenyl)cyclobutyl]acetonitrile (9.5 g) prepared as described above in dry tetrahydrofuran (25 ml) was added dropwise. The temperature of the mixture was allowed to rise to 0° C. and the mixture was stirred for ten minutes before a solution of methyl iodide (10 ml) in tetrahydrofuran (10 ml) was added. Tetrahydrofuran (75 ml) was added to give a homogeneous solution and a further solution of methyl iodide (4 ml) in tetrahydrofuran (10 ml) added. The mixture was stirred at ambient temperature for two hours and then water (50 ml) added. The aqueous phase was washed with ether and the ether combined with the organic phase of the reaction mixture. The combined organic phases were washed three times with 5N hydrochloric acid, three times with water, dried and evaporated to yield an oil which solidified and was recrystallised from industrial methylated spirit to give 2-[1-(4-chlorophenyl)cyclobutyl]-2-methylpropionitrile (m.p. 73°-75° C.).

The nitrile prepared above (4 g) was heated under reflux with potassium hydroxide (8 g) in diethyleneglycol (40 ml) for 24 hours. The reaction mixture was cooled, added to water (50 ml) and the aqueous phase washed twice with ether. The aqueous phase was acidified with 5N hydrochloric acid and extracted with three portions of ether. The combined ether extracts were washed with water, dried and evaporated to give a white solid which was recrystallised from petroleum ether (b.p. 60°-80°) to give 2-[1-(4-chlorophenyl)cyclobutyl]-2-methylpropionic acid (m.p. 95°-110° C.).

Oxalyl chloride (10 ml) was added to the acid (2 g) prepared as above and after the initial effervescence had subsided the mixture was heated under reflux for one hour. Excess oxalyl chloride was removed by distillation and the residual oil added to concentrated aqueous ammonia (75 ml). An oily solid formed which was extracted into ethyl acetate. The extract was washed with water, dried and evaporated to give 2-[1-(4-chlorophenyl)cyclobutyl]-2-methyl propionamide.

The amide prepared as above (1.34 g) was dissolved in a mixture of acetonitrile (8 ml) and water (8 ml) and iodosobenzene bistrifluoroacetate (3.4 g) added and the mixture stirred at ambient temperature for five and a half hours. Water (75 ml) and concentrated hydrochloric acid (8 ml) were added and the mixture extracted with ether. The ether extract was washed with 5N hydrochloric acid and the aqueous phase basified and extracted with further portions of ether which were dried and evaporated to give an oil. The oil was dissolved in petroleum ether (b.p. 80°-100°) and dry hydrogen chloride gas passed through the solution. 1-[1-(4-Chlorophenyl)cyclobutyl]-1-methylethylamine hydrochloride (m.p. 257°-259° C.) was collected by filtration (Formula I $R_1$, $R_2$=Me; $R_3$, $R_4$=H; $R_5$=4—Cl; $R_6$=H).

EXAMPLE 14

The product of Example 4(h) (3.4 g) was mixed with anhydrous sodium formate (0.72 g), 98% formic acid (10 ml) and 37–40% aqueous formaldehyde solution (5 ml) and the mixture heated at a temperature of 85°-95° C. for sixteen hours. The mixture was diluted with water (50 ml) and basified to pH 10 with aqueous sodium hydroxide solution. The basic aqueous solution was extracted with ether, washed with water and dried with magnesium sulphate. Dry hydrogen chloride gas was bubbled through the ether extract to give a white precipitate of N,N-dimethyl-1-[1-(4-chloro-3-trifluoromethylphenyl)cyclobutyl]ethylamine hydrochloride (m.p. 246°-247° C.) (Formula I $R_1$=Me; $R_2$=H; $R_3$, $R_4$=Me; $R_5$=4—Cl and $R_6$=3—$CF_3$).

EXAMPLE 15

The production of salts of the compounds of the invention is illustrated by the following Examples in which equimolar amounts of the base and the acid were taken up in a solvent. The salt was then obtained from the solution by conventional techniques.

| Example | Base | Acid | Solvent | m.p. of salt |
|---|---|---|---|---|
| 15(a) | 10(s) | citric | aqueous acetone | 158–160° |
| 15(b) | 10(s) | maleic | ether | 155–157° |
| 15(c) | 10(s) | succinic | ether | 152–155° |
| 15(d) | 2 | L(+)tartaric | I.M.S. | 150–153° |
| 15(e) | Note (a) | citric | ether/methanol | 163–164°(dec) |

(a) The base was 1-[1-(3,4-dimethylphenyl)cyclobutyl]-3-methylbutylamine prepared in a similar manner to that described in Example 10.

EXAMPLE 16

A solution of bromobenzene (15.7 g) in ether (50 ml) was added dropwise with cooling to magnesium turning (2.4 g) under an atmosphere of nitrogen. A solution of 1-(4-chlorophenyl)-cyclobutanecarbonitrile (19.1 g) prepared in a similar manner to that described in Example 1 for the 1-(3,4-dichlorophenyl)cyclobutane carbonitrile in ether (50 ml) was added and the ether replaced by dry toluene (130 ml). The reaction mixture was heated on a steam bath for one hour. A sample (20 ml) of the resulting solution was added to a solution of sodium borohydride (1 g) in diethyleneglycoldimethyl ether (60 ml) and the mixture was stirred for one and a half hours. Water (60 ml) was added slowly and the aqueous layer extracted with toluene. The toluene extracts were washed with water, dried and evaporated to give a residue which was dissolved in methanol (50 ml). 6N Hydrochloric acid (5 ml) was added and the soltution filtered and evaporated. Trituration with dry acetone gave α-[1-(4-chlorophenyl)cyclobutyl]benzylamine hydrochloride (m.p. 277°-279° C.) (Formula I $R_1$=Ph; $R_2$=H; $R_3$, $R_4$=H; $R_5$=4—Cl; $R_6$=H).

EXAMPLE 17

Methyl formate (62 ml) was added dropwise to isopropylamine (85.5 ml) with stirring at a rate which maintained gentle reflux conditions. Stirring was continued for two hours after the addition. Methanol was distilled off at 100° C. and N-isopropylformamide (b.p. 108°-109° C./25 mm Hg) obtained by distillation.

1-Acetyl-1-(4-chlorophenyl)cyclobutane (10.4 g) prepared in a similar manner to that described in Example 1 for 1-acetyl-1-(3,4-dichlorophenyl)cyclobutane and 98% formic acid (5 ml) were added to N-isopropylformamide (43.5 g) and the mixture heated at 180° C. for four hours. Excess starting material was distilled off under reduced pressure (20 mm Hg) to leave a viscous residue which was heated under reflux with concentrated hydrochloric acid (30 ml) for six hours. The reaction mixture was washed with ether until a colourless solution was obtained. The aqueous phase was basified, extracted with ether, dried and evaporated to give an oil which was dissolved in 5N hydrochloric acid. On evaporation a yellow oil was obtained which was triturated with petroleum ether (b.p. 62°-68° C.) to give N-isopropyl-1-[1-(4-chlorophenyl)cyclobutyl]ethylamine hydrochloride (m.p. 170°-174° C.) (Formula I $R_1$=Me; $R_2$=H; $R_3$=isopropyl; $R_4$=H; $R_5$=4—Cl; $R_6$=H).

EXAMPLE 18

1-Acetyl-1-(3,4-dichlorophenyl)cyclobutane (7.0 g) prepared as described in Example 1 was slowly added to a mixture of pyrrolidine (25 ml) and 98% formic acid (15 ml) heated to 130°-135° C. for five hours. The mixture was stirred and heated at 160°-165° C. for sixteen hours. After cooling the mixture was poured into 5N hydrochloric acid (200 ml). The solution was washed with ether, basified with aqueous sodium hydroxide solution and extracted with ether. The ether extract was washed with water, dried and hydrogen chloride gas was passed into the extract which was then evaporated to dryness. The residue was triturated with dry ether to give a solid which was recrystallised from propan-2-ol to give N-1-[1-(3,4-dichlorophenyl)cyclobutyl]ethyl pyrrolidine hydrochloride (m.p. 233°-235° C.) (Formula I $R_1$=Me; $R_2$=H; $R_3$ and $R_4$ together with the nitrogen to which they are attached form a pyrrolidine ring; $R_5$=4—Cl and $R_6$=3—Cl).

EXAMPLE 19

1-(4-Chlorophenyl)-1-cyclobutane carboxylic acid (10.5 g) prepared as described in Example 13 was heated under reflux with thionyl chloride (20 ml) for 2½ hours. Excess thionyl chloride was evaporated off and the acid chloride of the above acid distilled (b.p. 82°-96°/0.2 mm Hg).

A solution of the acid chloride (23.0 g) in dry tetrahydrofuran (100 ml) was added slowly to the product of the reaction of magnesium turnings (3.0 g) and ethyl bromide (12.0 g) in dry tetrahydrofuran at a temperature of −70 to −60° C. The temperature was kept at −60° C. for an hour and was then allowed to rise to 0° C. Water (50 ml) was added followed by 5N hydrochloric acid (150 ml) with cooling. The reaction mixture was extracted with ether, washed with water, sodium bicarbonate solution, dried. The solvent was removed by evaporation and 1-propionyl-1-(4-chlorophenyl)cyclobutane obtained by distillation (b.p. 96°-104° C./0.25 mm)

The ketone produced above was converted to N,N-dimethyl-1-[1-(4-chlorophenyl)cyclobutylpropylamine hydrochloride (m.p. 213°-215° C.) in a similar manner to that described in Example 12 (Formula I $R_1$=Et; $R_2$=H; $R_3$, $R_4$=Me; $R_5$=4—Cl; $R_6$=H).

EXAMPLE 20

1-Acetyl-1-(4-chlorophenyl)cyclobutane (61 g prepared in a similar manner to that described in Example 1 for 1-acetyl-1-(3,4-dichlorophenyl)cyclobutane, platinum oxide (0.75 g), 33% solution of methylamine in ethanol (60 g) and ethanol (30 ml) were charged into an autoclave. The autoclave was filled with hydrogen and maintained at about 60° C. and 20 bar pressure for ten hours. The reaction mixture was filtered through charcoal and the solids washed with absolute alcohol. The solvents were removed by evaporation and a sample of the residue (10 g) was shaken with 2M hydrochloric acid (50 ml) and ether (50 ml). The aqueous layer was basified and extracted with ether. The ether extract yielded a liquid on evaporation which was distilled (109° C./0.3 mm Hg) to give N-methyl-1-[1-(4-chlorophenyl)cyclobutyl]ethylamine (Formula I $R_1$=Me; $R_2$=H; $R_3$=Me; $R_4$=H; $R_5$=4—Cl and $R_6$=H).

EXAMPLE 21

Sodium borohydride (2.0 g) was added to solution of 1-[1-(3,4-dichlorophenyl)cyclobutyl]ethylamine (1.5 g prepared by treating the product of Example 1 with aqueous sodium hydroxide) in glacial acetic acid (30 ml). The mixture was heated at 95°-100° C. for sixteen hours and then cooled. Aqueous sodium hydroxide solution was added and the reaction mixture extracted with ether. The ether extract was shaken with 5N hydrochloric acid and the aqueous layer was washed with ether, basified and extracted with ether. Hydrogen chloride gas was passed into the ether extract which was evaporated to dryness. Trituration with acetone gave N-ethyl-1-[1-(3,4-dichlorophenyl)cyclobutyl]ethylamine hydrochloride (m.p. 211°-212° C.) (Formula I $R_1$=Me; $R_2$=H; $R_3$=Et; $R_4$=H; $R_5$=4—Cl and $R_6$=3—Cl.)

EXAMPLE 22

A mixture of N-ethyl-1-[1-(3,4-dichlorophenyl)cyclobutyl]ethylamine (0.5 g prepared by treating the product of Example 21 with aqueous sodium hydroxide) and acetic anhydride (1 ml) was heated at 40°-45° C. for thirty minutes. The reaction mixture was basified and extracted with ether. The ether extract was washed, dried and evaporated to give N-acetyl-N-ethyl-1-[1-(3,4-dichlorophenyl)cyclobutyl]ethylamine as an oil.

This oil was dissolved in tetrahydrofuran (10 ml) and borane-dimethylsulphide complex (0.5 ml) added dropwise. The reaction mixture was stirred at room temperature for two hours and then heated to 35°-40° C. for thirty minutes. After cooling the reaction mixture was basified and extracted with ether. Hydrogen chloride gas was passed into the dried ether extract which was evaporated to dryness. Trituration with ether gave N,N-diethyl-1-[1-(3,4-dichlorophenyl)cyclobutyl]ethylamine hydrochloride (m.p. 199°-201° C.). (Formula I $R_1$=Me; $R_2$=H; $R_3$, $R_4$=Et; $R_5$=4—Cl and $R_6$=3—Cl).

EXAMPLE 23

A mixture of 1-acetyl-1-(3,4-dichlorophenyl)cyclobutane (2.2 g) prepared as described in Example 1, ammonium acetate (7 g), sodium cyanoborohydride (0.4 g) and methanol (28 ml) was stirred at room temperature for four days. The reaction mixture was poured into a mixture of ice and water and the resulting mixture extracted with ether. The ether extract was washed with water, dried and the ether removed to leave 1-[1-(3,4-dichlorophenyl)cyclobutyl]ethylamine as an oil which was identified by standard analytical techniques as the compound of Example 1 in the form of its free base.

EXAMPLE 24

A mixture of 1-acetyl-1-(3,4-dichlorophenyl)cyclobutane (4.86 g) prepared as described in Example 1, hydroxylamine hydrochloride (1.6 g), sodium acetate trihydrate (3.3 g), industrial methylated spirit (15 ml) and water (2 ml) was heated under reflux for twenty hours. The cooled reaction mixture was poured into water and the oil which separated was cooled to give a solid which was recrystallised from industrial methylated spirit to give 1-acetyl-1-(3,4-dichlorophenyl)cyclobutane oxime (m.p. 120°-121° C.).

A solution of the oxime prepared above (4.0 g) in ether (50 ml) was added slowly to a stirred suspension of lithium aluminium hydride (0.9 g) in ether (50 ml) under nitrogen. The mixture was heated under reflux for one hour and, after cooling, water and then a 20% aqueous solution of Rochelle's salt (potassium sodium tartrate tetrahydrate) (27 ml) and a 10% aqueous solution of sodium hydroxide (6 ml) added. The reaction mixture was stirred for one hour and then continuously extracted with ether during eighteen hours. The ether extract was dried and the ether removed to leave a solid from which 1-[1-(3,4-dichlorophenyl)cyclobutyl]ethylamine was separated by high pressure liquid chromatography. The product was identified by standard analytical techniques as the compound of Example 1 in the form of its free base.

EXAMPLE 25

A 1M solution of diisobutylaliminohydride in hexane (200 ml) was added under nitrogen to a solution of 1-phenyl-1-cyclobutane carbonitrile (31.4 g) in either (100 ml) at a temperature below −30° C. The temperature was maintained below 0° C. for thirty minutes and 5N hydrochloric acid (200 ml) at a temperature of −10° C. added. The reaction mixture was washed with petroleum ether (b.p. 60°-80° C.) and then warmed to 40° C. The reaction mixture was extracted with petroleum ether (b.p. 60°-80° C.) and the extract dried and evaporated to yield 1-phenyl-1-cyclobutane-carbaldehyde as an oil.

Methylamine was bubbled through a solution of the aldehyde (9.4 g) prepared as above in toluene (100 ml) whilst the temperature of the reaction mixture was maintained below 0° C. Magnesium sulphate (20 g) which had been dried over a flame and then cooled under nitrogen was added to the reaction mixture which was left for sixteen hours at room temperature before being filtered. The toluene was then removed by evaporation and the residue dissolved in ether (50 ml). This solution was added to a solution of propyllithium prepared by slowly adding excess propyl bromide (12.8 g) to a suspension of lithium (1.26 g) in ether (50 ml). The resulting mixture was left for sixteen hours at room temperature. A trace of unreacted lithium was removed by filtration and the filter washed with ether, water and then 5N hydrochloric acid. The filtrate and washings were heated on a steam bath for one hour. After cooling the reaction mixture was washed with ether and the aqueous layer was basified using aqueous sodium hydroxide solution. The reaction mixture was extracted with ether and the extract dried and the ether removed to give a residue from which N-methyl-1-(1-phenylcyclobutyl)butylamine (b.p. 80°-86°/0.1 mm Hg.) was distilled.

The amine (2.3 g) prepared as described above was dissolved in ether (40 ml) and hydrogen chloride gas passed through the solution to precipitate N-methyl-1-(1-phenylcyclobutyl)butylamine hydrochloride (m.p. 196°-197° C.). (Formula I $R_1$=propyl; $R_2$=H; $R_3$=Me; $R_4$, $R_5$ and $R_6$ are H.)

EXAMPLE 26

A solution of 1-(3-chloro-5-methylphenyl)-1-cyclobutanecarbonitrile (8.0 g) in ether (40 ml) was added to a solution of propyl magnesium bromide [prepared by the reaction of 1-bromopropane (6.7 g) and magnesium (1.3 g)] in ether (80 ml) and the mixture heated under reflux for two and a half hours. Two thirds of the ether was evaporated off and then, after cooling, a solution of sodium borohydride (3.5 g) in ethanol (150 ml) added. The mixture was maintained at 50° C. for one hour and water (50 ml) and then 5N hydrochloric acid (50 ml) added. The ether layer was separated, dried and evaporated to yield a solid which was recrystallised from propan-2-ol to give 1-[1-(3-chloro-5-methylphenyl)cyclobutyl]butylamine hydrochloride (m.p. 145°-146° C.).

The hydrochloride salt prepared as above was shaken with ether and 5N sodium hydroxide solution and the ether layer evaporated to give the primary amine which was converted into N,N-dimethyl-1-[1-(3-chloro-5-methylphenyl)cyclobutyl]butylamine hydrochloride (m.p. 148° C.) (Formula I $R_1$=propyl; $R_2$=H; $R_3$ and $R_4$=Me; $R_5$=3—Cl and $R_6$=5—Me) in a similar manner to that described in Example 2.

EXAMPLE 27

1-Acetyl-1-(3,4-dichlorophenyl)cyclobutane prepared as described in Example 1 (4.86 g) and cyclohexylamine (2.28 ml) were heated and stirred under reflux for 30 minutes. Stirring and heating was continued on an oil bath at 145° C. for 3 hours. The product was cooled to ambient temperature, dissolved in methanol (50 ml) and sodium borohydride (0.8 g) added. The mixture was stirred at ambient temperature for twenty hours and then poured into water and the resulting mixture extracted with ether. The ether extract was washed with water and dried. After removal of the solvent N-cyclohexyl-1-[1-(3,4-dichlorophenyl)cyclobutyl]ethylamine (b.p. 144°–156°/0.6 mm Hg) was obtained by distillation (Formula I $R_1$=Me; $R_2$=H; $R_3$=cyclohexyl; $R_4$=H; $R_5$=4—Cl; $R_6$=3—Cl).

EXAMPLE 28

Pharmaceutical compositions containing any one of the compounds of formula I disclosed in Examples 1 to 27 are prepared in the following manner.

EXAMPLE 28(a)

Tablets are prepared from the following ingredients:

|  | Parts by Weight |
| --- | --- |
| Active Ingredient | 50.0 |
| Lactose | 78.5 |
| Polyvinylpyrrolidone | 5.0 |
| Maize Starch | 15.0 |
| Magnesium Stearate | 1.5 |

The active ingredient, the lactose and some of the starch are mixed and granulated with a solution of the polyvinylpyrrolidone in ethanol. The granulate is mixed with the stearic acid and the rest of the starch and the mixture is compressed in a tabletting machine to give tablets containing 50.0 mg. of the active ingredient.

EXAMPLE 28(b)

Capsules are prepared in the following way. A mixture of the active ingredient (45 parts by weight) and lactose powder (205 parts by weight) is filled into hard gelatin capsules, each capsule containing 45 mg. of the active ingredient.

EXAMPLE 28(c)

In the preparation of enteric coated tablets, the tablets described in Example 28(a) are given a thin coat of shellac varnish, followed by 20 coats of cellulose acetate phthalate in a manner well known in the art. In a similar manner the capsules of Example 28(b) may be provided with an enteric coating.

EXAMPLE 28(d)

Vials containing a solution of water-soluble compounds of the present invention suitable for injection are prepared from the following ingredients:

| Active Ingredient | 1100 g. |
| --- | --- |
| Mannitol | 1100 g. |
| Water, freshly distilled | to 11 liters |

The active ingredient and mannitol are dissolved in some of the water and the volume of the solution is adjusted to 11 liters. The resulting solution is sterilised by filtration and filled into sterile vials each containing 1.65 ml. of solution.

EXAMPLE 28(e)

In the preparation of suppositories, 100 parts by weight of the finely ground active ingredient is incorporated in 1214 parts by weight of triglyceride suppository base and the mixture is formed into suppositories each containing 100 mg. of the active ingredient.

In the preceding Examples novel ketones of formula V have been disclosed in which $R_1$, $R_5$ and $R_6$ have the meaning given in Examples 1, 1(a) to 1(e), 3, 4, 4(a) to 4(e), 6, 7, 7(a) to 7(d) 9, 9(a) to 9(n), 10, 10(a) to 10(z), 10(aa), 10(bb), 11(i), 11(k) and 11(l). These novel ketones of formula V are prepared by hydrolysis of novel imines of formula XI in which Y=MgBr and $R_1$, $R_5$ and $R_6$ have the meaning given in the Examples specified above.

In the preceding Examples novel cyano compounds of formula XII are disclosed in which $R_5$ and $R_6$ have the meaning given in Examples 1, 1(d), 1(e), 4(g), 9(e), 9(m), 10(k), 10(e), 10(p), 10(r), 10(v), 10(y), 10(z), 10(aa), 10(bb), 11(k), 11(l) and 26.

In the preceding Examples novel formamides of formula XVII are disclosed in which $R_1$, $R_3$, $R_5$, $R_6$, $R_7$, $R_8$ have the meaning given in Examples 1, 1(a) to 1(e), 3, 4, 4(a) to 4(e), 6, 7, 7(a) to 7(d), 9, 9(a) to 9(n), 10, 10(a) to 10(z), 10(aa), 10(bb), 11(i), 11(k), 11(l).

We claim:

1. A compound of formula III

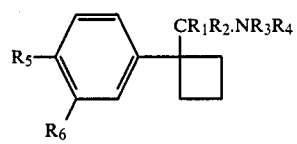

or a pharmaceutically acceptable salt thereof in which $R_1$ is methyl or ethyl, $R_2$ is H or methyl, $R_3$ and $R_4$ are each selected from the group consisting of H, methyl and ethyl, or $R_3$ is a cycloalkyl group containing 3 to 6 carbon atoms and $R_4$ is H, or $R_3$ and $R_4$ together with the nitrogen atom to which they are attached form a pyrrolidinyl ring, and $R_5$ and $R_6$ together with the phenyl ring to which they are attached form a 4-chlorophenyl, 4-bromophenyl, 4-iodophenyl, 3-chlorophenyl, 3-bromophenyl, 3,4-dichlorophenyl, 4-chloro-3-fluorophenyl, 4-chloro-3-trifluoromethylphenyl, 4-biphenylyl, 2-naphthyl or 2-phenanthryl group.

2. A compound according to claim 1 which is N-methyl-1-[1-(3,4-dichlorophenyl)cyclobutyl]ethylamine or a pharmaceutically acceptable salt thereof.

3. A compound according to claim 1 which is 1-[1-(4-chlorophenyl)cyclobutyl]ethylamine or a pharmaceutically acceptable salt thereof.

4. A compound according to claim 1 which is N-methyl-1-[1-(4-chlorophenyl)cyclobutyl]ethylamine or a pharmaceutically acceptable salt thereof.

5. A compound according to claim 1 which is N,N-dimethyl-1-[1-(4-chlorophenyl)cyclobutyl]ethylamine or a pharmaceutically acceptable salt thereof.

6. A compound according to claim 1 or a pharmaceutically acceptable salt thereof in which $R_1$ is methyl; $R_2$ is H; $R_3$ is H, methyl or ethyl; $R_4$ is H, methyl or ethyl; $R_5$ is chloro; $R_6$ is H or chloro.

7. A compound according to claim 6 which is 1-[1-(3,4-dichlorophenyl)cyclobutyl]ethylamine or a pharmaceutically acceptable salt thereof.

8. A compound according to claim 6 which is N,N-dimethyl-1-[1-(3,4-dichlorophenyl)cyclobutyl]-ethylamine or a pharmaceutically acceptable salt thereof.

9. A pharmaceutical composition useful for treating depression in humans which comprises an antidepressently effective amount of a compound of the formula III

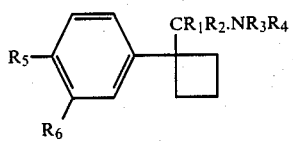

or a pharmaceutically acceptable salt thereof in which $R_1$ is methyl or ethyl, $R_2$ is H or methyl, $R_3$ and $R_4$ are each selected from the group consisting of H, methyl and ethyl, or $R_3$ is a cycloalkyl group containing 3 to 6 carbon atoms and $R_4$ is H, or $R_3$ and $R_4$ together with the nitrogen atom to which they are attached form a pyrrolidinyl ring, and $R_5$ and $R_6$ together with the phenyl ring to which they are attached form a 4-chlorophenyl, 4-bromophenyl, 4-iodophenyl, 3-chlorophenyl, 3-bromophenyl, 3,4-dichlorophenyl, 4-chloro-3-fluorophenyl, 4-chloro-3-trifluoromethylphenyl, 4-biphenylyl, 2-naphthyl or 2-phenanthryl group, in combination with a pharmaceutically acceptable carrier.

10. A composition according to claim 9 in which N-methyl-1-[1-(3,4-dichlorophenyl)cyclobutyl]ethylamine or a pharmaceutically acceptable salt thereof.

11. A composition according to claim 9 which is 1-[1-(4-chlorophenyl)cyclobutyl]ethylamine or a pharmaceutically acceptable salt thereof.

12. A composition according to claim 9 which is N-methyl-1-[1-(4-chlorophenyl)cyclobutyl]ethylamine or a pharmaceutically acceptable salt thereof.

13. A composition according to claim 9 which is N,N-dimethyl-1-[1-(4-chlorophenyl)cyclobutyl]ethylamine or a pharmaceutically acceptable salt thereof.

14. A composition according to claim 9 wherein $R_1$ is methyl, $R_2$ is H, $R_3$ is H, methyl or ethyl, $R_4$ is H, methyl or ethyl, $R_5$ is chloro and $R_6$ is H or chloro.

15. A composition according to claim 14 wherein the compund is 1-[1-(3,4-dichlorophenyl)cyclobutyl]ethylamine or a pharmaceutically acceptable salt thereof.

16. A composition according to claim 14 wherein the compound is N,N-dimethyl-1-[1-(3,4-dichlorophenyl)cyclobutyl]-ethylamine or a pharmaceutically acceptable salt thereof.

17. A method of treating depression in humans which comprises administering to a human or animal in need thereof an antidepressently effective amount of a compound of the formula III

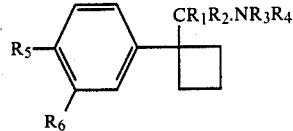

or a pharmaceutically acceptaable salt thereof in which $R_1$ is methyl or ethyl, $R_2$ is H or methyl, $R_3$ and $R_4$ are each selected from the group consisting of H, methyl and ethyl, or $R_3$ is a cycloalkyl group containing 3 to 6 carbon atoms and $R_4$ is H, or $R_3$ and $R_4$ together with the nitrogen atom to which they are attached form a pyrrolidinyl ring, and $R_5$ and $R_6$ together with the phenyl ring to which they are attached form a 4-chlorophenyl, 4-bromophenyl, 4-iodophenyl, 3-chlorophenyl, 3-bromophenyl, 3,4-dichlorophenyl, 4-chloro-3-fluorophenyl, 4-chloro-3-trifluoromethylphenyl, 4-biphenylyl, 2-naphthyl or 2-phenanthryl group, in combination with a pharmaceutically acceptable carrier.

18. A method according to claim 17 wherein $R_1$ is methyl, $R_2$ is H, $R_3$ is H, methyl or ethyl, $R_4$ is H, methyl or ethyl, $R_5$ is chloro and $R_6$ is H or chloro.

19. A method according to claim 17 in which N-methyl-1-[1-(3,4-dichlorophenyl)cyclobutyl]ethylamine or a pharmaceutically acceptable salt thereof.

20. A method according to claim 17 which is 1-[1-(4-chlorophenyl)cyclobutyl]ethylamine or a pharmaceutically acceptable salt thereof.

21. A method according to claim 17 which is N-methyl-1-[1-(4-chlorophenyl)cyclobutyl]ethylamine or a pharmaceutically acceptable salt thereof.

22. A method according to claim 17 which is N,N-dimethyl-1-[1-(4-chlorophenyl)cyclobutyl]ethylamine or a pharmaceutically acceptable salt thereof.

* * * * *

UNITED STATES PATENT AND TRADEMARK OFFICE
CERTIFICATE OF CORRECTION

PATENT NO. : 4,767,790

DATED : August 30, 1988

INVENTOR(S) : James E. Jeffery; Antonin Kozlik; Eric C. Wilmshurst

It is certified that error appears in the above-identified patent and that said Letters Patent is hereby corrected as shown below:

On the face of the patent, under "References Cited", the following should appear:

FOREIGN PATENT DOCUMENTS 973887 10/1964 United Kingdom
1530172 10/1978 United Kingdom

OTHER PUBLICATIONS

Chem. Abs., 87, 23236s-Synthesis of Novel Cyclic & Acyclic Sulphamides.
Chem. Abs., 85, 32678y-Aminoesters of 1-(Alpha-Naphthyl) Cycloalkane-1-Carboxylic Acids and 1-(Alpha-Napthyl) Cycloalkane-1-Methyl Guanidines in Russian and copy of English translation attached.
Arya and Shenoy-Synthesis of New Heterocycles, Indian Journal of Chemistry, 14B, 766-769 (1976).
Armyanskii Khimichesdii Zhurnal, 29, No. 2, 194-199 (1976).
"Neurotransmitters and Drugs", by Kruk and Pycock, Croom Helm London, p. 149.
Nieforth and Cohen, "Central Nervous System Stimulants", Chapter 13 of the book entitled Principles of Medicinal Chemistry, by Foye, Second edition, Lea & Febiger, 1981, Phil., pp. 303-316.
Israel Journal of Chemistry 13 No. 2 (1975), pp. 125-136, A. Kalir, "1-Phenylcycloalkylamine Derivatives III".
"1-Phenylcycloalkylamine Derivatives, II. Synthesis and Pharmacological Activity", A. Kalir, (1969), pp. 473-477, of vol. 12, J. Med Chem.
Kalir, et al., 1-Phenylcycloalkylamine Derivatives I, Israel Journal of

UNITED STATES PATENT AND TRADEMARK OFFICE
CERTIFICATE OF CORRECTION

PATENT NO. : 4,767,790

DATED : August 30, 1988

INVENTOR(S) : James E. Jeffery; Antonin Kozlik; Eric C. Wilmshurst

It is certified that error appears in the above-identified patent and that said Letters Patent is hereby corrected as shown below:

Chemistry 5 (1967), pp. 223-229. --.

Signed and Sealed this

Sixth Day of June, 1989

Attest:

DONALD J. QUIGG

Attesting Officer

Commissioner of Patents and Trademarks